United States Patent [19]
Paul et al.

[11] Patent Number: 5,719,178
[45] Date of Patent: Feb. 17, 1998

[54] METHODS AND COMPOSITIONS FOR TREATING ATTENTION-DEFICIT/ HYPERACTIVITY DISORDER

[76] Inventors: Julie Chasen Paul, 2010 Centennial Ct., Ballwin, Mo. 63011; Steven Joseph Tenenbaum, 384 Littany La., Chesterfield, Mo. 63017

[21] Appl. No.: 559,645

[22] Filed: Nov. 20, 1995

[51] Int. Cl.$^6$ .................. A61K 31/35; A61K 31/335
[52] U.S. Cl. .................. 514/450; 514/453; 514/456
[58] Field of Search .................. 514/456, 450, 514/453

[56] References Cited

U.S. PATENT DOCUMENTS 3,436,407  4/1969  Masquelier .................. 549/400
4,698,360  10/1987  Masquelier .................. 514/456

OTHER PUBLICATIONS

Alexopoulos, Medline #91288300, Psychiatric Clinics of North America, 1991, vol. 14(2), pp. 327–340.
Williams, Medline #89316118, Primary Care; Clinics in Office Practice, 1989, vol. 16(2), pp. 451–474.
Reifler, Medline #87058644, J of the American Geriatrics Society, 1986, vol. 34(12), pp. 855–859.
Priest, Medline #95233116, Acta Psychiatrica Scandinavica, 1995, vol. 386, pp. 40–43.
Reynolds, Medline #96157665, International Psychogeriatrics, 1995, 7 Suppl 27–39.
Flint, Medline #95129028, Canadian J of Psychiatry, 1994, vol. 39 (8Suppl 1), S9–18.
Reynolds, Medline #92394911, J of Clinical Psychiatry, 1992, vol. 53 Suppl 45–53.
Passwater, Richard A., Ph.D., *The Second International Pycnogenol Symposium*, May 1995, pp. 126–137.
M.W. International, Inc., *The whole truth about Pycnogenol*.
Passwater et al., *Pycnogenol The Super "Protector" Nutrient*, 1994.

*Primary Examiner*—Alan L. Rotman
*Assistant Examiner*—D. Margaret M. Mach
*Attorney, Agent, or Firm*—John N. Bain; Raymond J. Lillie; William Squire

[57] ABSTRACT

A regimen and composition for treating Attention Deficit/ Hperactivity Disorder (ADHD) by the use of proanthocyanidin both with and without a heterocyclic anti-depresssant, preferably desipramine and a citrus bioflavinoid.

11 Claims, No Drawings

METHODS AND COMPOSITIONS FOR TREATING ATTENTION-DEFICIT/HYPERACTIVITY DISORDER

The invention relates to the treatment of Attention Deficit/Hyperactivity Disorder ("ADHD") generally and specifically methods and compositions for treating ADHD by use of proanthocyanidin in a controlled regimen both with and without a heterocyclic antidepressant, preferably desipramine and a citrus bioflavinoid.

BACKGROUND OF INVENTION

ADHD is extensively described in *Diagnostic and Statistical Manual of Mental Disorders*, Fourth Edition, American Psychiatric Association, Washington, D.C., 1994 beginning on page 78. Persons suffering from ADHD exhibit a persistent pattern of inattention and/or hyperactivity-impulsivity that is more frequent and severe than typically observed in persons at a comparable level of development. Three subtypes are recognized: ADHD, Combined Type; ADHD, Predominantly Inattentive Type; and ADHD, Predominantly Hyper-active-Impulsive Type. The Predominantly Inattentive Type is characterized by failure to give close attention to details, making careless mistakes in various tasks, messy and carelessly performed work product exhibiting a lack of considered thought. Such individual soften have difficulty sustaining attention in tasks or play activities and find it difficult to persist with tasks until completion. They often appear as if their mind is elsewhere or as if they are not listening or did not hear what has just been said. This last characteristic is frequently referred to as "spacey" in clinical practice. Tasks that require sustained mental effort are experienced by such individuals as unpleasant and, consequently typically avoided.

The predominantly Hyperactive-impulsive subtype is characterized by fidgetiness, excessive unproductive movement when inappropriate such as fidgeting with objects, tapping hands, shaking legs or feet, excessive talking or making noise. Symptoms in adults or adolescents frequently take the form of feelings of restlessness and difficulty in engaging in quiet sedentary activities.

On the other hand, impulsivity manifests itself as impatience, difficulty in delaying responses, blurting out answers before questions have been completed, difficulty awaiting one's turn, frequently interrupting or intruding on others, making comments out of turn, failing to listen to directions, initiating conversations at inappropriate times, grabbing objects form others, touching things they are not supposed to touch and clowning around.

Depending on the age and developmental stage of the individual, ADHD sufferers may exhibit low frustration tolerance, temper outbursts, bossiness, stubbornness, excessive and frequent insistence that requests be met, mood lability, demoralization, dysphoria, rejection by peers, and poor self-esteem. Obviously, the disorder can seriously adversely impact social, educational and vocational development and performance.

There are no established diagnostic laboratory tests in the clinical assessment of ADHD. It is not yet entirely clear what fundamental cognitive deficit is responsible for the abnormal effortful mental processing exhibited in ADHD.

For many years, ADHD, irrespective of subtype, has been treated by the mild central nervous system stimulant, methylphenidate hydrochloride, known as Ritalin. Regrettably, Ritalin is associated with frequent, undesirable side-effects including nervousness and insomnia, hypersensitivity (including skin rash, urticaria, fever, arthralgia, exfoliative dermatitis, erythema multiform with histopathological findings of necrotizing vasculitis, and thrombocytopenic purpura), anorexia, nausea, dizziness, palpitation, headache, dyskinesia, drowsiness, blood pressure and pulse changes, both up and-down; tachycardia, angina, cardiac arrhythmia, abdominal pain and weight loss during prolonged therapy. There have been rare reports of Tourette's syndrome as a side effect of Ritalin which is particularly regrettable since ADHD is sometimes associated with Tourette's syndrome. Although ADHD frequently manifests before six years of age, Ritalin should not be used in children under six years since safety and efficacy in this age group have not been established.

Ritalin, when taken in the morning, loses its effectiveness toward late afternoon, yet if taken then, frequently results in insomnia. Thus, symptoms return in the evening but cannot be treated with Ritalin.

ADHD also frequently produces an excessive emotional response to various stimuli most commonly found in the predominantly hyperactive-impulsive subtype. Ritalin and other stimulants, whether strong or weak, such as the amphetamines and caffeine, do not generate the emotional buffering or filtering necessary to both delay and attenuate excessive emotional response.

Strong CNS stimulants such as the amphetamines are not generally recommended for ADHD.

Caffeine, a weak stimulant, used alone, has not been found particularly useful in the treatment of ADHD although adult victims frequently use caffeine, generally as found in tea and coffee as an adjunct.

SUMMARY OF INVENTION

A method for treating ADHD comprising a daily regimen of taking by mouth, a quantity of proanthocyanidin derived from pine bark in a quantity sufficient to relieve symptoms of ADHD but not to exceed approximately 0.625 mg per kg of body weight per dose, every approximately 3.5 to 4.0 hours during the time attenuation of symptoms of ADHD is desired and preferably in addition thereto taking by mouth a quantity of a heterocyclic antidepressant, preferably desipramine in quantities sufficient to attenuate ADHD-related symptoms of lack of cognitive focus.

DESCRIPTION OF INVENTION

U.S. Pat. No. 4,698,360 discloses a proanthocyanidin derived from conifer bark as a therapeutic agent with a radical scavenger effect useful in treating cerebral involution troubles in the elderly, hypoxia following atherosclerosis, tumors or other illnesses generated by free radicals. Such a proanthocyanidin is commercially available from Now Foods of Glendale, Ill. under the tradename of Pycnogenol. U.S. Pat. No. 3,456,407 discloses a method for extracting proanthocyanidins from pine bark. As used herein, the term "proanthocyanidin(s)" and "pycnogenol" refers to the extract from conifer bark meeting the criteria of U.S. Pat. No. 4,698,360.

In the present invention, the only useful proanthocyanidin is that derived from conifer bark preferably pine bark such as the back of the maritime pine. Pycnogenol is sold by Now Foods in a capsule containing thirty (30) milligrams of Pycnogenol and three hundred (300) milligrams of a citrus bioflavinoid. Alleged substitutes for Pycnogenol such as that derived from grape seeds, has not been found effective for the purposes of the present invention.

It has been found that Pycnogenol, alone, taken in a regimen of multiple, spaced-apart doses separated by a specific limited range of time, containing a limited range of Pycnogenol concentration is useful in treating ADHD without the side-effects of Ritalin. It has also been found that Pycnogenol taken in accordance with the above regimen together with a heterocyclic antidepressant such as desipramine is particularly useful in treating ADHD with symptoms of "spaciness" or lack of cognitive focus. Additionally, the regimen of the present invention is effective without the concomitant use of caffeine or other stimulants.

The preferred regimen in accordance with the present invention comprises taking approximately 2.0 mg of Pycnogenol per kilogram of body weight per day divided into four equal doses every 3.5 to 4.0 hours, beginning from on or about waking to 8 or 9 a.m. The lower limit of Pycnogenol is that which produces the desired effect which may be somewhat variable depending upon the individual. The upper limit is approximately 2.5 mg per kg of body weight per day divided into four equal doses. If the upper limit is exceeded, symptoms common to excessive stimulation through artificial or natural stimulants results such as Ritalin or blue Green Algae. The optimum daily dose is approximately 0.50 to 0.60 mg. per kg of body weight per day divided into four equal doses. Greater than optimal doses may bring about a tendency to withdraw, lethargy, increased irritability and/or increased edginess and agitation.

It has also been found that excessive stimulation results if an upper limit of approximately 0.625 mg of Pycnogenol per dose is exceeded.

Another regimen in accordance with the present invention comprises the above regimen of Pycnogenol together with desipramine in an effective quantity, preferably in spaced-apart doses either with or between doses of Pycnogenol. For instance, it has been found that 10 mg of desipramine three times per day has been particularly effective in attenuating "spaciness" for an adult weighing 120 lbs. This dose of desipramine is substantially less than the recommended usual adult dose of 100 to 200 mg per day for the treatment of depression.

It has been common practice for individuals exhibiting ADHD to take the equivalent of five or more cups of coffee per day for the stimulant effect of its caffeine. It has been found that the above two regimens permit but does not require to take the equivalent of two cups of undecaffeinated coffee per day.

The amount of Pycnogenol in each dose and the total daily dose is important to producing the desired effect on ADHD without undesirable side effects. If the upper limit of Pycnogenol is exceeded, the patient becomes eddy or even so unfocused or spacey as to be "zombie-like." If less than an effective amount of Pycnogenol is taken, the effect on ADHD is insufficient to be clinically significant or acceptable. In starting treatment, it has been found that a target of 0.54 mg of Pycnogenol per day should be employed. If found effective, it should be continued because there is little value in trying to find a "lower limit" of effectiveness. Moreover, at this dose, undesirable side effects are not experienced. If this dose is not effective an increased but spaced regimen of equal doses should be initiated within the upper limit specified herein.

The time limit between doses is also important to achieve the desired results. The effect of the Pycnogenol wears off after 3.5 to 4.0 hours and symptoms rapidly return at the dose limits indicated. Nevertheless, on a 3.5 to 4 hour regimen, if taken at 6 to 8 AM, and last taken at 6:30 PM, the effect will persist until at least 10:30 PM and not result in insomnia or other undesirable side-effects. The four hour regimen can be employed for persons need in the effect for a longer waking period but if greater than four hours is employed, the symptoms of ADHD will likely return between doses.

EXAMPLES

The following examples are presented as illustrative of the invention disclosed and claimed herein.

Example 1

This example is predicated on a 120 lb adult who experiences ADHD, predominantly of the hyperactive subtype.

30 mg of Pycnogenol were taken four times per day every 3.5 hours beginning at approximately 8 AM. Two cups of non-decaffeinated coffee per day are tolerated but unnecessary.

The symptoms of ADHD were reduced to such an extent that they did not adversely affect either function or general comfort. No insomnia was experienced nor symptoms of over stimulation. There was no need for any other stimulants.

Example 2

This example is predicated on a 120 lb adult who experiences ADHD, combined type, who also experiences "spaciness" if untreated.

30 mg of Pycnogenol were taken four times per day every 3.5 to 4 hours beginning at approximately 6 to 8 AM. Additionally, 10 mg of desipramine were taken 3 times per day with the first three doses of Pycnogenol spaced-apart every 4 hours beginning at approximately 8 AM.

The symptoms of ADHD were reduced to such an extent that they did not adversely affect either performance or comfort. In particular, it prevented "spaciness" and permitted the subject to clearly cognitively focus during the entire waking day without experiencing insomnia or symptoms of over stimulation. As in Example 1, the subject tolerated but did not need two cups of undecaffeinated coffee per day. Caffeine in adults may improve sleep/arousal problems con, non in ADHD, but likely needs to be limited due to its compounding the effects of the Pycnogenol.

Example 3

This example is also predicated on a 120 lb adult suffering from ADHD, combined type both with and without symptoms of "spaciness."

The regimens of both examples 1 and 2 were employed but the Pycnogenol was compounded with 300 mg of a citrus bioflavinoid with the same results in each case except that the symptoms of spaciness were not relieved as effectively with the use of Pycnogenol without the concomitant use of desipramine.

Example 4

This example is also predicated on a 120 lb adult suffering from ADHD of the predominantly inattentive subtype. The regimen of Example 1 was employed successfully suppressing the symptoms such that they did not interfere with either function or comfort. No insomnia was experienced. The use of moderate amounts of non-decaffeinated coffee were tolerated but not required.

Example 5

This example is predicated on the subject of Example 4 with the exception that the Pycnogenol was compounded with 300 mg of a citrus bioflavinoid. Results were experienced as set forth in Example 4.

Example 6

As a control, a subject as in Example 2, took five cups of coffee per day together with 10 mg of desipramine three times per day without significant attenuation of the symptoms of ADHD particularly the spaciness and having only a limited calming effect.

Example 7

As another control, a subject as in Example 2 took 90 mg of Pycnogenol in midmorning and drank five cups of non-decaffeinated coffee per day as well as other caffeinated beverages. By the fourth day, the subject began experiencing muscle tightening and tingling on the left side of the face which the subject had also experienced with Ritalin in combination with caffeine and Blue Green Algae in combination with caffeine. While taking the Pycnogenol, the symptoms of ADHD were significantly reduced, however, the side effects were uncomfortable. The subject reduced the amount of Pycnogenol to 30 mg per day together with the equivalent of five cups of undecaffeinated coffee per day. The subject began to increase the amount of Pycnogenol to 90 mg per day while reducing the amount of caffeine equivalent to two cups of coffee per day and experienced improvement in the symptoms of ADHD and experienced alleviation of the side effects. A regimen of 30 mg of Pycnogenol three times per day every 4 to 5 hours was tried with some significant success in relieving symptoms but the symptoms returned between doses, particularly in the late evening. When the regimen of Example 1 was initiated, symptoms were substantially relieved without reoccurrence either between doses or in the late evening.

The successful regimens set forth above within the limits both as to dose and spacing should be effective for children under the age of six years and can be used with subjects suffering from Tourette's syndrome as well as ADHD.

We claim:

1. A method for treating ADHD comprising a daily regimen of taking by mouth, a quantity of proanthocyanidin extracted from a conifer bark in a quantity sufficient to relieve symptoms of ADHD but not to exceed approximately 0.625 mg per kg of body weight per dose, every approximately 3.5 to 4.0 hours during the time attenuation of symptoms of ADHD is desired.

2. A method for treating ADHD comprising the regimen in accordance with claim 1 wherein the daily upper limit of the proanthocyanidin is approximately 2.0 mg per kg of body weight.

3. A method for treating ADHD comprising the regimen in accordance with any one of claims 1 or 2 in which approximately 300 mg of a citrus bioflavinoid is taken with each dose of the proanthocyanidin.

4. A method for treating ADHD comprising the regimen in accordance with any one of claims 1 or 2 and taking an antidepressant in a quantity just sufficient to attenuate ADHD-related symptoms of lack of cognitive focus.

5. A method for treating ADHD comprising the regimen in accordance with any one of claims 1 or 2 and taking a heterocyclic antidepressant in a quantity just sufficient to attenuate ADHD-related symptoms of lack of cognitive focus.

6. A method for treating ADHD comprising the regimen in accordance with any one of claims 1 or 2 and taking a tricyclic antidepressant in a quantity just sufficient to attenuate ADHD-related symptoms of lack of cognitive focus.

7. A method for treating ADHD comprising the regimen in accordance with any one of claims 1 or 2 and taking desipramine in a quantity just sufficient to attenuate ADHD-related symptoms of lack of cognitive focus.

8. A method for treating ADHD comprising the regimen in accordance with claim 7 in which the desipramine is taken in an amount of approximately 30 mg per day.

9. A method for treating ADHD comprising the regimen in accordance with claim 7 in which the desipramine is taken in an amount of approximately 0.55 mg per kg of body weight per day.

10. A method for treating ADHD comprising the regimen in accordance with claim 9 in which the desipramine is taken in three equal doses per day.

11. A method for treating ADHD comprising the regimen in accordance with claim 7 in which each dose of the proanthocyanidin is taken with approximately 300 mg of a citrus bioflavinoid.

* * * * *

UNITED STATES PATENT AND TRADEMARK OFFICE
CERTIFICATE OF CORRECTION

PATENT NO.  : 5,719,178

DATED       : February 17, 1998

INVENTOR(S) : Paull, et. al.

It is certified that error appears in the above-identified patent and that said Letters Patent is hereby corrected as shown below:

Title page, item [19] and [76], inventor's last name should read – Paull --.

Signed and Sealed this

Twenty-eighth Day of April, 1998

Attest:

BRUCE LEHMAN

*Attesting Officer*  *Commissioner of Patents and Trademarks*